United States Patent [19]

Saville

[11] Plant 5,097

[45] Sep. 6, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 382,400

[22] Filed: May 27, 1982

[51] Int. Cl.[3] ..... A01H 5/00

[52] U.S. Cl. ..... Plt./9

[58] Field of Search ..... Plt./9

*Primary Examiner*—James R. Feyrer

*Attorney, Agent, or Firm*—Vincent G. Gioia

[57] ABSTRACT

A new miniature rose variety of near Neyron rose coloring appearing to lighten upon aging.

1 Drawing Figure

The present invention relates to a new and distinct variety of rose plant of the miniature rose class, which was originated by my crossing as seed parent my seedling of (Little Darling×Tiki) and the rose known as "Party Girl" as pollen parent. The denomination of the new rose is "Savahowdy".

Among the novel characteristics possessed by this new variety which distinguish it from its parent and all other varieties of which I am aware are unusual near Neyron rose coloring similar in bud form, in coloring and shape to the hybrid tea rose Tiffany. The flowers have a salmon toned petal undersurface. Asexual reproduction by budding of the new variety as performed in Essex County, Mass., shows that the foregoing and other distinguishing characterstics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "50B" is plate 50B of The Royal Horticultural Society Colour Chart.

Parentage: Seedling.

*Seed parent.*—My unpatented, unreleased seedling of (Little Darling×Tiki).

*Pollen parent.*—"Party Girl".

Class: Miniature.

The following observations are made of specimens grown under glass in Essex County, Mass. during the month of March.

FLOWER

Blooming habit: Recurrent.

A. Bud:

(1) *Size.*—Medium.

(2) *Form.*—Pointed to urn shaped with slightly depressed center.

(3) *Color.*—After sepals fall, salmon colored petal undersurface (near 27A with pink cast) of main portion of the petal is first visible, however, claret rose 50B colored petal edge of the petal undersurface may also be seen.

(4) *Sepals.*—Longer than bud, slightly foliated.

(5) *Peduncle.*—Length — about $\frac{7}{8}$ to 1 inch. Aspect — straight. Strength — erect. Color — near 145A.

B. Bloom:

(1) *Size.*—Average size when fully expanded — about $1\frac{1}{2}$ inches.

(2) *Borne.*—Singly and small sprays.

(3) *Form.*—High centered, petals quill to points.

(4) *Petalage.*—Number of petals under normal conditions — about 25.

(5) *Color.*—As pointed buds open they become urn shaped and reveal more Rhodonite red 51C to 51D exposed petal upper surfaces. However, petal color lightens to Empire rose 50D but combining in overall effect with salmon color 27A cast of petal undersurface, seen best in flowers at $\frac{1}{3}$ open stage, to display a neyron rose 56A to 55D tonality. As flowers open further to about $\frac{1}{2}$ open stage color appears 56C to 56D but continues to salmon colored cast as long as petal undersurfaces are seen.

C. Petals:

(1) *Texture.*—Thick.

(2) *Appearance.*—Inside velvety, outside satiny.

(3) *Form.*—Fan shaped with rounded edges (before quilling).

(4) *Arrangement.*—Regularly arranged, shingle-like.

(5) *Petaloids in center.*—Few.

(6) *Persistence.*—Drop off cleanly.

(7) *Fragrance.*—Slight.

(8) *Lasting quality.*—Very long lasting on plant and as cut flower.

REPRODUCTIVE ORGANS

A. Stamens, filaments and anthers:

(1) *Arrangement.*—Stamens regularly arranged around styles.

(2) *Color.*—Near 17C.

B. Pollen:

*Color.*—Near 17B.

C. Styles: Even, medium length.

D. Stigmas:

*Color.*—Near 159C.

E. Hips: None observed.

PLANT

A. Form: Upright.

B. Growth: Vigorous, somewhat open.

*Height attained.*—About 14 to 16 inches.

C. Foliage: Compound 5 to 7 leaflets.

(1) *Size.*—Medium.

(2) *Quantity.*—Average.

(3) *Color.*—New foliage: Upper side — near to 138A; Under side — near to 144A. Old foliage: Upper side — near 138A; Under side — near 144A.

(4) *Shape.*—Oval.

(5) *Texture.*—Upper side is semi-glossy and under side is matte.

(6) *Edge.*—Serrated.

(7) *Serration.*—Uniform.

(8) *Leaf stem.*—Color — near to 183D. Under side — near 144A.

(9) *Stipules.*—Medium, slightly bearded.

(10) *Resistance to disease.*—Blackspot — average. Mildew — average. Rust — average.

D. Wood:

(1) *New wood.*—Color — near 144C. Bark — smooth.

(2) *Old wood.*—Color — near 146B. Bark — smooth.

E. Thorns:

(1) *Thorns.*—Quantity (main stalk) — ordinary. On laterals from stalk — normal. Form — long, thin, straight. Length — medium. Color — near 185C. Position — scattered.

(2) *Prickles.*—None.

F. Winter hardiness: Needs protection in severe climate.

I claim:

1. A new and distinct variety of rose plant of the miniature rose class, substantially as shown and described, characterized particularly by unusual near Neyron rose coloring having a salmon colored petal undersurface which appears to lighten as flowers open.

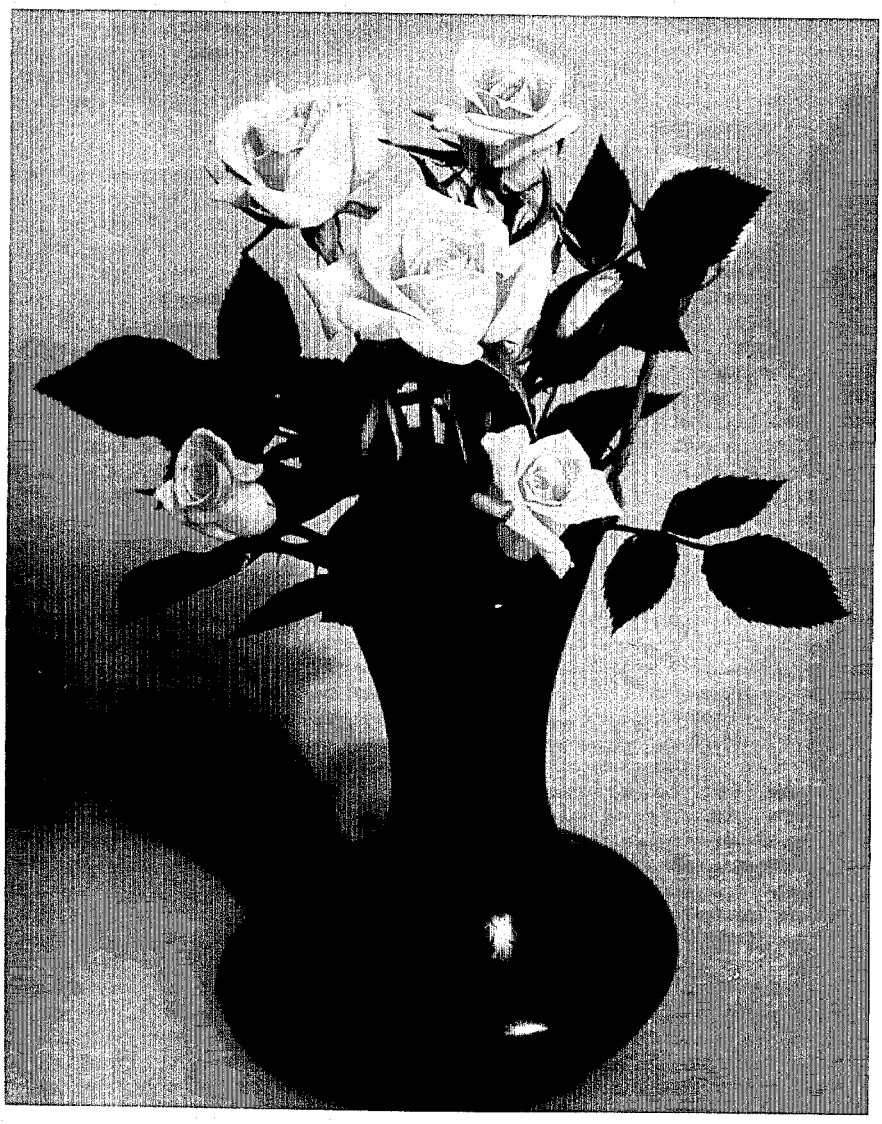

* * * * *